United States Patent [19]

Blossfeld et al.

[11] Patent Number: 5,185,773
[45] Date of Patent: Feb. 9, 1993

[54] METHOD AND APPARATUS FOR NONDESTRUCTIVE SELECTIVE DETERMINATION OF A METAL

[75] Inventors: Daniel H. Blossfeld, Walled Lake; Eric W. Schneider, Shelby Township, Macomb County, both of Mich.

[73] Assignee: General Motors Corporation, Detroit, Mich.

[21] Appl. No.: 732,525

[22] Filed: Jul. 19, 1991

[51] Int. Cl.⁵ .............................. G01N 23/06
[52] U.S. Cl. .......................... 378/53; 378/51; 378/54
[58] Field of Search .......... 378/51, 53, 54, 44, 378/45, 50, 86, 88, 89, 124, 143

[56] References Cited
U.S. PATENT DOCUMENTS 3,114,832 12/1963 Alvarez .......................... 378/124
4,048,496 9/1977 Albert ........................... 578/124

OTHER PUBLICATIONS

R. Jenkins and J. L. DeVries, "Practical X-Ray . . . 2nd Edition", 1969, pp. 12 through 16 and p. 185.
M. A. Short & S. Bonfiglio, "Energy . . . Detectors", NBS Spec., Publ. #604, issued Mar. 1981, pp. 391 ∝ 415.
C. D. Radcliffe, B. Angle, E. S. Macias, and P. P. Gaspar, "Gold . . . Rays", Archaeometry, 22, 1 (1980) pp. 47–55.
Eric W. Schneider and Gerald L. Vaneman, "The . . . Converters", 1986, Int'l Cong. SAE Tech. Paper Series 860567.

Primary Examiner—David P. Porta
Attorney, Agent, or Firm—George A. Grove

[57] ABSTRACT

An amount and distribution of platinum dispersed on a catalyst carrier is determined by generating at least two energy components of lead x-rays by fluorescence of lead with gadolinium or cobalt and directing the x-rays onto a surface of the carrier and then determining an amount of platinum based upon relative attenuation of the two energy components of lead x-rays proportional to a relative amount of platinum thereon.

8 Claims, 6 Drawing Sheets

Pb K- RATIO FOR Pt FOIL CONVERTERS

LENGTH, mm

METHOD AND APPARATUS FOR NONDESTRUCTIVE SELECTIVE DETERMINATION OF A METAL

FIELD OF THE INVENTION

This invention relates to a method for determining an amount and distribution of a metal dispersed on a substrate and, in particular, for determining platinum dispersed on ceramic and metal foil catalytic converters.

BACKGROUND OF THE INVENTION

Platinum is one of the primary elements used to reduce emissions. Platinum is dispersed on a carrier in a catalytic converter of a vehicle and a reduction of emission occurs when exhaust gases contact platinum on the surface of the catalytic converter. Thus, it is desirable to disperse the platinum as uniformly as possible on the catalytic converter.

A radioisotopic two-scan technique is currently in use which measures the distribution of noble metal on catalytic converters. However, such techniques require a scan both before and after application of the platinum in order to determine the distribution of platinum, by difference between the two scans.

Electromagnetic (gamma and x-rays) have been used for single-scan elemental analysis, for example to analyze the gold content of an object using a barium isotope. This analysis method for determining gold is not suitable for platinum because platinum cannot be detected using barium.

Thus, it would be advantageous to have a single scan technique which would reduce analysis time, which would be platinum specific, and which would not be affected by the presence of other elements co-deposited with platinum on a substrate such as a catalytic converter.

SUMMARY OF THE INVENTION

There is provided a method and apparatus for the specific measurement of platinum based on the relative attenuation of at least two energy components of electromagnetic radiation generated by fluorescence of lead. The two energy components have different absorption characteristics for platinum but similar absorption characteristics for other components. The method may also be used for specific determination of other metals such as gold, mercury and iridium. Since in the process of manufacturing catalytic converters it is not expected that gold, mercury and iridium will be present, the technique may be used to accurately and efficiently determine the quantity and distribution of platinum in and on a catalytic converter. As used herein, reference to a quantity and/or an amount of metal or platinum includes zero metal or platinum within limits of detectability. Advantageously, the method may also be used to simultaneously determine the distribution of a washcoat layer on the catalytic converter. The washcoat layer is often referred to as a carrier or substrate.

In a general method for determining an amount of metal selected from platinum, gold, iridium and mercury, first at least two energy components of lead x-rays are generated. At least one component is above and at least one other component is below the K-absorption edge of the metal to be detected. The components are generated by fluorescence of lead with a source of radiant energy greater than a K-absorption edge characteristic of lead. The x-rays are then directed to a surface of the substrate containing the metal to be determined. Then, an amount of metal may be determined based upon a relative attenuation of two or more energy components of the lead x-rays. In a preferred method, two energy components of lead x-rays, one above and one below a K-absorption edge characteristic of the metal to be detected, are used. Relative attenuation based on more than two components is also possible but not necessary. That is, accurate results are achievable with two components.

In a preferred method, platinum is determined by fluorescing lead with gadolinium (Gd-153) providing two energy components, one above and one below the K-absorption edge of platinum. The two characteristic lead x-rays generated from Gd-153 have energies of approximately 75 and 84 keV which bracket 78 keV K-absorption edge of platinum. The 84 keV x-ray component will be attenuated to a much greater degree than the 75 keV x-ray component, and the relative attenuation ratio of the two components of x-rays is related to an amount of platinum, including an amount of zero, or the absence of platinum.

In a preferred apparatus, the Gd-153 source and a lead plate fluorescent target are positioned together and constructed and arranged so that the detection of lead x-rays is maximized while the detection of Gd-153 gamma-rays incident on the target is minimized. The object to be analyzed, such as a catalytic converter, is placed preferably on a moving rack between two collimators. The detector is preferably connected to a data collector such as a personal computer for automatic analysis. Preferably, the detector is a germanium detector of high resolution satisfactory to resolve the two x-ray components. In use, preferably at least two components of x-rays are generated essentially simultaneously so as to be simultaneously incident on a desired location of the object to be analyzed. Alternatively, the energy components may be generated separately.

In a preferred method, a catalytic converter having an unknown amount of platinum at a location thereon is analyzed based on a relative attenuation of the two energy components, as compared to attenuation by a known standard quantity of platinum. Therefore, the quantity of an unknown amount of platinum may be determined proportional to the ratio of the relative attenuations produced by the unknown amount and the known quantity of platinum.

The method and apparatus conveniently provide nondestructive testing of a substrate to determine an amount of platinum by a single scan of the substrate.

These and other objects, features and advantages will become apparent from the following description of the preferred embodiments, appended claims and accompanying drawings.

DETAILED DESCRIPTION OF THE PREFERRED EMBODIMENTS

Figure 1:
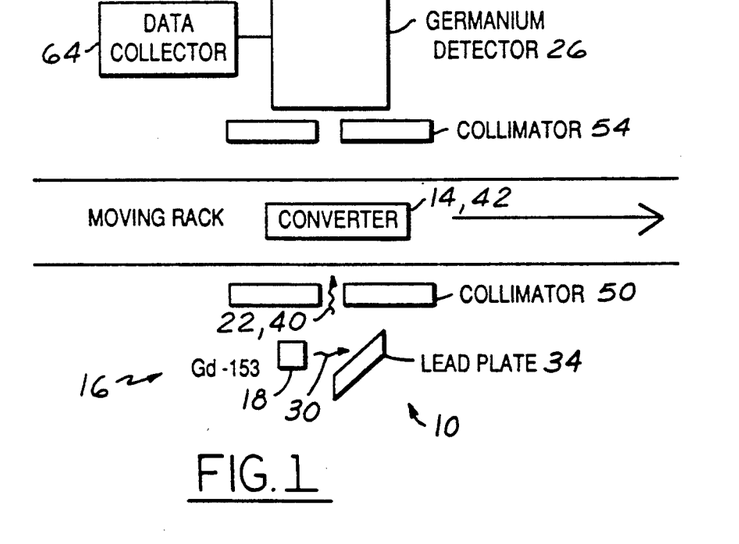
FIG. 1 is a schematic of the apparatus embodying the invention and showing the arrangement between the source of lead x-rays, the object to be analyzed, and the detector.

FIG. 1 illustrates an apparatus 10 embodying this invention with an object 14 to be analyzed placed between a source 16 of two radiant energies of lead (Pb) x-rays 22 and a detector 26 that measures the intensity of the two energies 22. The radiant energy generated by the source 16 is preferably produced using isotopes of gadolinium-153 or cobalt-57.

Preferably, the gadolinium-153 (Gd-153) source 18, with gamma-rays 30 of energies at 97.4 and 103.2 keV, is used to bombard a lead plate fluorescent target 34 to provide a beam 40 of the lead x-rays 22 having at least first and second energy components, respectively, about 75 and about 84 keV. Each energy component of the Gd-153 is greater than a K-absorption edge characteristic of lead which is at 88.00 keV. Desirably, the gadolinium radioactive isotopes are supplied to the target 34 in the range of 20 to 300 mCI and preferably 225 mCI, in order to analyze an object 14 such as a catalytic converter 42.

The Gd-153 source 18 and the lead plate fluorescent target 34 are positioned in a configuration whereby the detection of lead x-rays 22 is maximized while the detection of GD-153 gamma-rays 30 is minimized. A first collimator 50 is placed in front of the lead plate target 34 and a second collimator 54 is placed in front of the detector 26. The first collimator 50 in front of the source 16 functions to form and direct or focus the beam 40. Preferably, the first collimator 50 is made of lead and the second collimator 54 is made of steel. The object 14 to be analyzed is placed preferably on a moving rack 60 between the collimators 50, 54. The detector 26 is preferably connected to a data collector 64 such as a personal computer for automatic data analysis. Preferably, the detector 26 is a germanium detector of high resolution satisfactory to resolve the two x-ray components.

In use, preferably, at least two components of x-rays 22 are generated essentially simultaneously so as to be simultaneously incident on a desired location of the object 14 to be analyzed. Alternatively, the energy components may be generated separately.

The method of the invention is based upon the relative attenuation of at least two energy components of electromagnetic radiation generated by the fluorescence of lead by the Gd-153 gamma-ray source. The energy components have different absorption characteristics for metals such as gold, platinum, mercury and iridium but similar absorption characteristics for other components.

In the method, the object 14 to be analyzed is placed between the source 18 of gamma-rays 30 and the detector 26. A decrease in the intensity with the object 14 present is due to partial absorption by the object 14 of some of the rays 22 of beam 40 passing through it. Therefore, the composition of an object 14 can be determined from absorption measurements. Advantageously, the beam 40 may include as few as two energy components of x-rays 22, and the composition of the absorbing object 14 can be determined from the intensity ratio of the first and second energy components.

Figure 2:
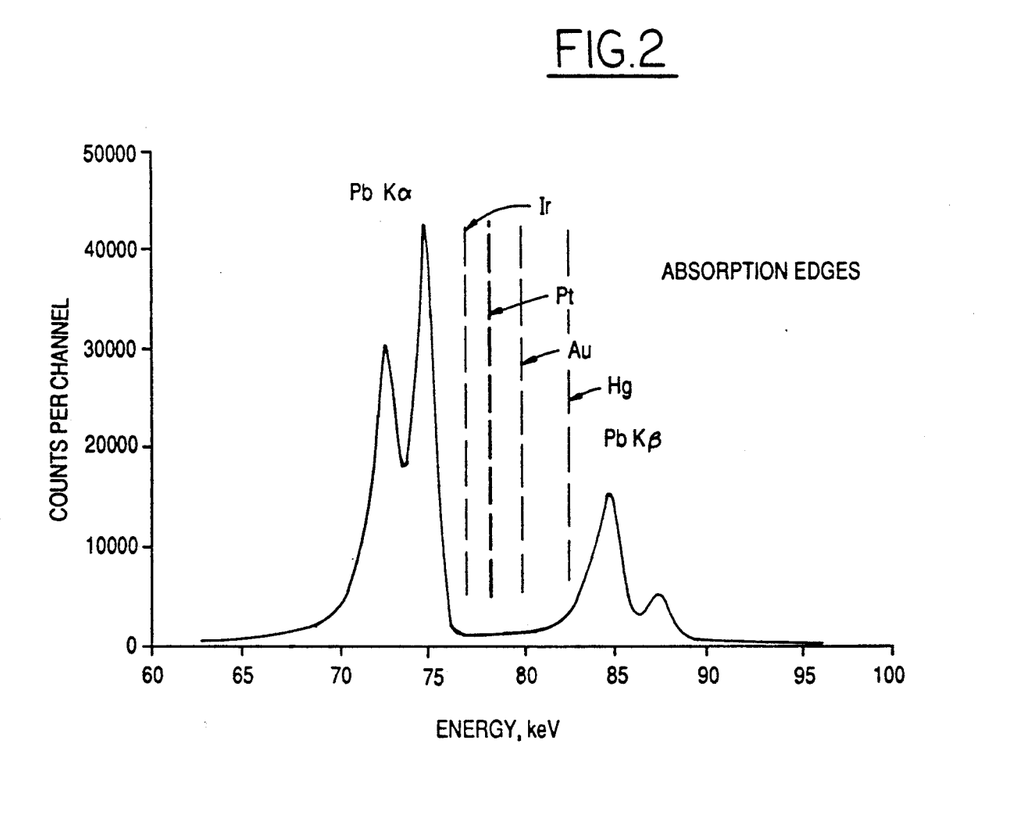
FIG. 2 is a lead x-ray spectrum as produced from the excitation of lead by a Gd-153 source.

The method is based on discontinuities in the absorption coefficient for radiation (gamma and x) rays at energies corresponding to the electronic binding energies of the absorber, such as a metal. One discontinuity in the absorption coefficient characteristic of an element is called the K-absorption edge. As shown in FIG. 2, the K x-ray absorption edge of selected metals is as follows: platinum at 78 keV, gold at 80 keV, mercury at 83 keV, and iridium at 76 keV, each represented by dashed lines of FIG. 2. The technique is specific for the presence of any one of the elements, platinum, gold, mercury or iridium. If a combination of the elements is present, the technique will detect the accumulated total and may not provide a discrete analysis for each.

Thus, for example, the method may be used to determine the presence of and the amount of platinum in a catalytic converter 42 if it is known that none of, or insignificant amounts of, the other metals (gold, mercury and iridium) are expected to be a part of the catalytic converter 42. The Gd-153 source may also be used for concurrent measurement of washcoat distribution on the catalytic converter 42.

The attenuation of x-rays by platinum increases by almost a factor of three when the K-absorption edge is crossed. The two characteristic lead x-rays generated from the Gd-153 source (energies of approximately 75 and 84 keV) are attenuated differently in the presence of platinum. The 84 keV x-ray was attenuated to a much greater degree than the 75 keV x-ray. The relative attenuated ratio of the two x-rays was used to determine an amount of platinum present in the catalytic converter 42. The weight of the converter 42 and the amount of washcoat loading of the converter 42 advantageously had no significant effect on the analysis of platinum. The method detects an amount or quantity of platinum, including zero platinum, if platinum is not detected within the limits of detectability.

Testing as described below confirmed that the ratio of the intensities of the x-rays transmitted through the converter 42 depended strongly on the concentration of platinum because the component with an energy above the x-ray K-absorption edge of platinum was absorbed much more strongly than the component with energy below the discontinuity.

The ratio of the intensities for the transmitted x-ray components is related to the amount of platinum in the absorber by a mathematical relationship. The general equation which describes the attenuation of electromagnetic (x or gamma) radiation through an absorber is:

$$ln(I/Io) = -upx \qquad (1)$$

where I and Io are the radiation intensities with and without material in the path of the beam, respectively; u is the mass absorption coefficient; p is the density or concentration of the absorbing species; and x is the thickness of the material.

Figure 3:
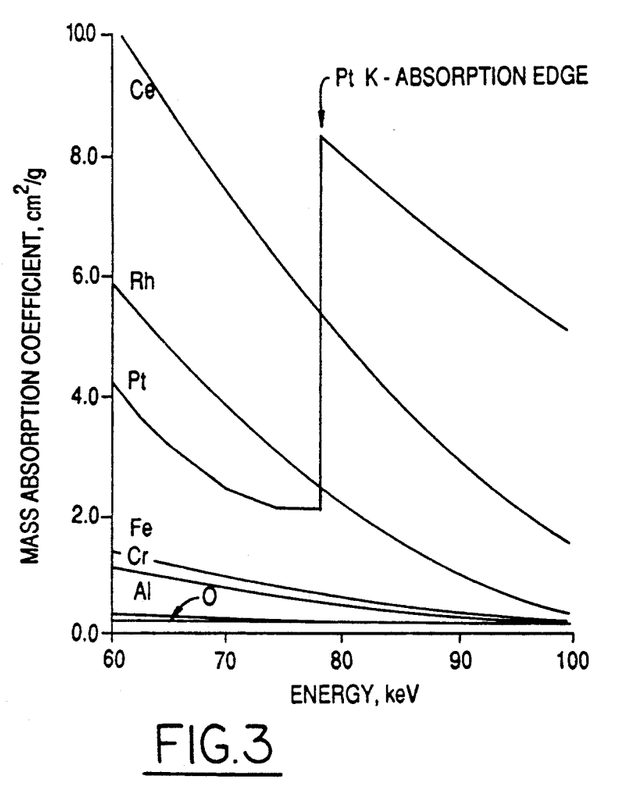
FIG. 3 is a diagram of mass absorption coefficients of selected elements versus energy.

The mass absorption coefficient, u, depends upon both the atomic number of the absorbing material and the energy of the electromagnetic radiation. FIG. 3 displays a plot of the mass absorption coefficient versus energy in the range of 60 to 100 keV for the major elemental constituents of a catalytic converter. These curves have been obtained by quadratic fits to tabulated values. In the case of Pt (Atomic Number, Z=78), values used to obtain the fits have been extrapolated from those tabulated for Au (Z=79).

In general, the value of u increases with Z and with decreasing energy. The large discontinuity in the absorption coefficient for Pt at 78.38 keV is termed its K-absorption edge. The value of this discontinuity is the energy required to promote a K-shell electron to a vacant level (or remove it from the atom). If the energy of the incoming radiation exceeds this minimum value, an additional absorption mechanism is available. Hence, the mass absorption coefficient shows a discontinuous increase above this energy.

In accordance with the method, radiation attenuation measurements made at two energies (one just below and one just above the K-absorption edge) provided differential absorption directly proportional to the amount of Pt present in the absorber. Since the two radiation energy components were very close, the relative absorption due to the amount of other elements present was minor. Therefore, the method provided selective Pt determination without the need for performing measurements before and after adding Pt to the catalytic converter 42.

In mathematical terms, Equation 1 can be rewritten as:

$$ln(I/Io) = -x \{summation\ of\ (u(i)\ p(i))\} \quad (2)$$

where i represents each element i in the absorber. And, for electromagnetic energy E(1), Equation 2 becomes:

$$ln\{I(E1)/Io(E1)\} = -x \{summation\ of\ (u(i)\ (E1)\ p(i))\} \quad (3)$$

where E(1) represents a radiation energy just below the Pt K-absorption edge. The density term, p(i), can be written as:

$$p(i) = W(i)/V; \quad (4)$$

where V is the volume of the sample, and W is the weight. Substituting into Equation 3 yields:

$$ln\{I(E1)/Io(E1)\} = -x/v \{sum\ of\ (u(i)\ (E1)\ w(i))\} \quad (5)$$

Likewise, a similar equation can be written for energy E(2), just above the Pt K-absorption edge:

$$ln\{I(E2)/Io(E2)\} = -x/v \{sum\ of\ (u(i)\ (E2)\ w(i))\} \quad (6)$$

By subtracting Equation 6 from Equation 5 and using the laws of logarithms on the left hand side;

$$ln\left[\frac{I(E2)/Io(E2)}{I(E1)/Io(E1)}\right] = \frac{-X}{V} [sum\ of\ \{u(i)(E2) - u(i)(E1)\}w(i)] \quad (7)$$

In the case where the two energy components E1 and E2 were close, the mass absorption coefficients for all elements except Pt did not change appreciably. Hence, Equation 7 simplified to:

$$ln\left[\frac{I(E2)/Io(E2)}{I(E1)/Io(E1)}\right] \approx \frac{-X}{V} \{u(Pt)(E2) - u(Pt)(E1)\}W(Pt) \quad (8)$$

Assuming all samples have the same thickness and volume, Equation 8 simplified to:

$$ln\left[\frac{\{I(E2)/Io(E2)\}}{\{I(E1)/Io(E1)\}}\right] \approx KW(Pt) \quad (9)$$

where K is a constant. Thus, measurements of radiation intensities with and without the sample in the path of the radiation beam are directly related to the quantity of Pt deposited.

As can be seen, Equations 7, 8 and 9 are based upon a difference in attenuation which is expressed as a log of the ratios of the intensities. In this case, the quantity of platinum is directly related to the difference in attenuation corrected by a constant, due to the simplifying assumptions described above.

Alternatively, Equation 6 can be divided by Equation 5 to yield:

$$\frac{ln\{I(E2)/Io(E2)\}}{ln\{I(E1)/Io(E1)\}} = \frac{sum\ of\ \{(u(i)(E2)w(i)\}}{sum\ of\ \{(u(i)(E1)w(i)\}} \quad (10)$$

The right-hand side of the equation can be separated into its individual terms as Equation (11) below:

$$\frac{ln\{I(E2)/Io(E2)\}}{ln\{I(E1)/Io(E1)\}} = \frac{u(Fe)(E2)W(Fe)}{sum\ of\ (u(i)(E1)W(i))} + \ldots + \frac{u(Pt)(E2)W(Pt)}{sum\ of\ (u(i)(E1)W(i))} \quad (11)$$

In a nominal metal-foil monolith (MFM) converter, the major absorbing elements are Fe and Ce, with the Pt term accounting for only about four percent of the total attenuation. Also, the Pt term in each denominator accounts for less than one percent of the summation. This is because of the low weight of Pt and the fact that E1 is below the Pt K-absorption edge. Therefore, when only the Pt weight is changed, Equation 11 simplifies to:

$$\frac{ln\{I(E2)/Io(E2)\}}{ln\{I(E1)/Io(E1)\}} \approx k1 + k2\{W(Pt)\} \quad (12)$$

And, again, intensity measurements can be related linearly to the weight of Pt deposited.

As can be seen, Equations 10, 11 and 12 are based upon a ratio of attenuation expressed as a ratio of the logs of the intensities of the two components. Again, the quantity of platinum is linearly related to the intensity measurements and adjusted by two constants.

Both Equation 9 and Equation 12 have been derived with the use of simplifying approximations. If Energies components E(1) and E(2) are very close, then Equation 9 is preferred because of its simplicity. However, depending on the extent of the difference in energies and the uncontrolled variation in the amount of other materials present, Equation 12 may be preferred. Calculations of the expected sensitivity for Pt using Equations 9 and 12 are presented below. Effects due to expected variations of other materials, based on the nominal elemental composition of catalytic converters and the radiation energy used in this work, are also included below.

The apparatus and method of the invention were used to determine the presence of platinum in catalytic converters 42 scanned by a beam 40 of x-rays 22 generated by the fluorescence of lead 34 with the high intensity gamma source 18 of Gd-153 and correlating the change in the ratio of lead x-rays 22 to the amount of platinum present. This was done in the absence of mercury, iridium and gold, so that the technique was specific for platinum in that platinum was the only element that affected the relative attenuation, expressed as Ka/Kb, and also as the "Pb K-ratio" as per Equation 12.

Seven metal foil monolith catalytic converters (MFM) and six ceramic catalytic converters were tested by the method and apparatus of the invention. The seven metal foil monoliths were oval shaped and 152 mm in length, 150 mm high × 80 mm wide.

Each MFM was coated with an alumina/ceria washcoat (79/21). Five of the seven MFMs contained platinum catalysts with a variety of weights. Two of the MFMs had no platinum.

All six of the ceramic converters were coated with alumina/ceria (72/28) washcoat, and three contained platinum catalysts. The three ceramic converters without catalysts had variable washcoat weights. The three ceramic converters with catalysts had similar washcoat weights but varied platinum weights.

A thin platinum foil, used for calibration, was applied to catalytic converters identified as D204 and #3, as indicated in Table 1. The thin platinum foil was purchased from AESAR (Seabrook, N.H.) and was a square shape about 50 mm on a side and about 0.00264 mm thick. All converters which included platinum contained rhodium equal to approximately one-fifth of the weight of platinum.

Catalytic converters prepared as described above are summarized in Table 1.

TABLE 1

| Converter Type | Number | Converter Weights | | |
|---|---|---|---|---|
| | | Uncoated, (g) | Washcoat, (g) | Platinum, (g) |
| MFM | 285-033 | 856 | — | — |
| MFM | 284-485 | 876 | 182 | — |
| MFM | 284-518 | 914 | 186 | 2.55 |
| MFM | 284-519 | 891 | 181 | 2.55 |
| MFM | #1 | 835 | 195 | 2.12 |
| MFM | #2 | 827 | 195 | 1.74 |
| MFM | #3 | 818 | 195 | 1.31 |
| Ceramic | D2 | 602 | 275 | — |
| Ceramic | D206 | 604 | 290 | — |
| Ceramic | D218 | 601 | 306 | — |
| Ceramic | D201 | 602 | 292 | 2.29 |
| Ceramic | D202 | 601 | 292 | 1.72 |
| Ceramic | D204 | 602 | 293 | 1.31 |

In order to test the accuracy of the method and apparatus, all weights were determined in advance. That is, the weight of the monolith was determined before and after coating, before and after adding platinum, and then correcting the platinum to rhodium ratio in order to determine as accurately as possible the amount of platinum added.

The catalytic converters 42 were scanned by the method and apparatus 10 of the invention using a 225 mCi source 18 to generate two energy components, E1, E2 of Pb x-rays 22 by fluorescence. A lead plate 34 was placed at a 45 degree angle with respect to the gamma-ray beam 30 so as to fluoresce the lead, yielding a beam 40 of lead x-rays 22 generally perpendicular to the converters 42 as shown in FIG. 1.

X-ray intensities were measured using a portable high-purity germanium detector 26 (EG & G Ortec). A collimator 54 of steel block was placed in front of the detector 26 to collimate the x-ray with a 10 mm slit width. Converters 42 were scanned as they passed through the beam 40 of x-rays 22.

Output of the germanium detector 26 was routed through a data collector 64 comprising an amplifier and a multi-channeled buffer card installed into a slot on an IBM personal computer. Special software was written to enable the computer to perform spectroscopic data acquisition and analysis. The data acquisition time was about two minutes for each measurement on a converter 42 with approximately 25 measurements comprising one converter scan. Thus, each converter 42 was scanned in about one hour.

In the method of the invention, the expected radiation attenuation of a typical MFM catalytic converter was calculated by determining values for equations described above based on the nominal compositions of catalytic converters and the absorption coefficients presented in FIG. 3. The MFM converter composition was taken as: 800 g of foil (75% Fe, 20% Cr, 5% Al), 190 g of alumina/ceria washcoat (83.3% Pt, 16.7% Rh).

Two energy component windows were used, 67–77 keV and 79–90 keV, which encompassed the two x-ray regions of interest. Energies selected for energy components $E(1)$ and $E(2)$ were 74.16 and 85.26 keV, respectively. These values represent averages of the two Pb Ka and the three Pb Kb energies, weighted by intensity (FIG. 2). The two major Ka peaks ($Ka1 = 74.97$, $Ka2 = 72.81$ keV) are just below the Pt K-edge, whereas the three unresolved Kb peaks ($Kb1 = 84.94$, $Kb2 = 87.30$, $Kb2 = 84.40$ keV) are just above the Pt K-edge.

With values calculated for Equations 5 and 6, the radiation intensity expressions in Equations 9 and 12 were determined. Results yield a nominal value of 0.6289 for Equation 9 and −1.557 for Equation 12. More importantly, change in the values of each expression were determined as a function of change in noble metal loading or changes in the amount of other materials present. Table 2 presents the predicted sensitivities of these expressions to changes in noble metal loading, foil weight, coating weight, and the coating composition.

TABLE 2

Sensitivity of Radiation Intensity Expressions to Changes In The Composition of FM Converter

| Material | Amount of Change | Change In Value | Error In Pt—Rh, % |
|---|---|---|---|
| Equation 9 | | | |
| Pt—Rh Catalyst | +/− 1 g | +/− 2.03 × 10−2 | — |
| Fe—Cr—Al Foil | +/− 10 g | −/+ 1.49 × 10−2 | −/+ 23.6% |
| Alumina Coat | +/− 10 g | −/+ 2.26 × 10−2 | −/+ 36.0% |
| Coating Comp. | +/− 1% CeO2 | −/+ 1.92 × 10−3 | −/+ 30.4% |
| Equation 12 | | | |
| Pt—Rh Catalyst | +/− 1 g | +/− PAT-3 | — |
| Fe—Cr—Al Foil | +/− 10 g | −/+ 2.85 × 10−4 | −/+ 1.6% |
| Alumina Coat | +/− 10 g | −/+ 2.31 × 10−4 | +/− 1.3% |
| Coating Comp. | +/− 1% | −/+ 3.04 × 10−4 | −/+ 1.7% |

TABLE 2-continued

Sensitivity of Radiation
Intensity Expressions to Changes In The
Composition of FM Converter

| Material | Amount of Change | Change In Value | Error In Pt—Rh, % |
|---|---|---|---|
| CeO2 | | | |

These calculations demonstrated several points. The first line in Table 2 showed that a change of plus or minus ($\pm$) 1 g in catalyst (nominal value of 3.11 g) resulted in only about a three percent change in the value of Equation 9 and a 0.4 percent change in Equation 12. Therefore, a system for quantitive measurement of Pt-Rh catalyst is provided with high statistical precision in the measurement of Pb Ka and Kb intensities.

The remaining three lines in Table 2 showed the effects of uncontrolled variations in foil, coating, and coating composition on Pt-Rh catalyst determination. The range selected for the amount of change represented reasonable control limits in the MFM product process. The calculations showed that Equation 12 resulted in a substantially lower error in the Pt-Rh value than Equation 9 as the amounts of the other constituents were changed. Thus, with the use of Equation 12, expected variations in these constituents do not effect the Pt-Rh determination significantly.

Experimental data presented herein demonstrated that Equation 12 results in much less fluctuation due to variations in foil and coating weight. Hence, all results presented below are based on the calculated radiation intensity expression in Equation 12, referred to as the "Pb K-ratio".

Figure 4:
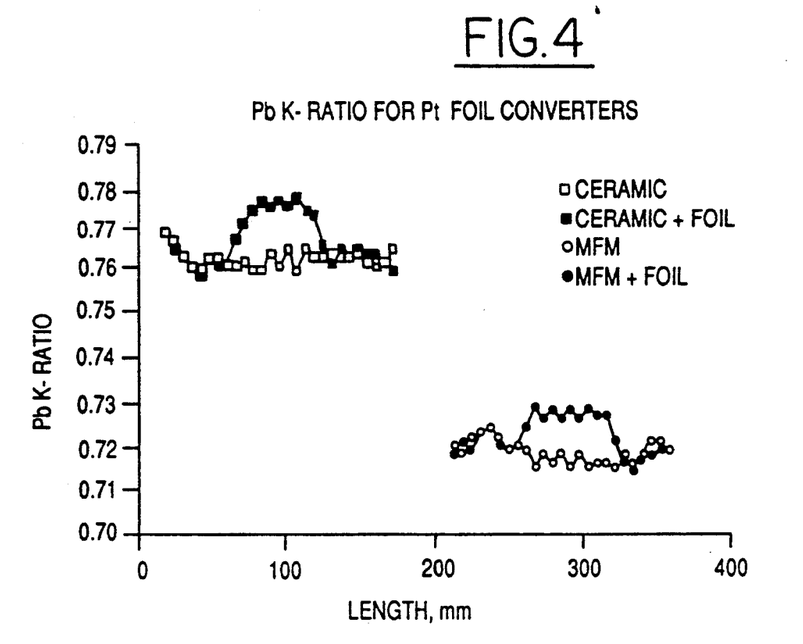
FIG. 4 is a diagram of lead K-ratios for selected metal foil monolith and ceramic converters with and without platinum foil attached.

Platinum foil scans were run on one ceramic and one MFM converter, D204 and #3, with the platinum foil taped to the center of the converter. These results are plotted in FIG. 4. The presence of the foil can be readily identified and displays good uniformity. The foil thickness was estimated to be equivalent to about 1 g of platinum.

Figure 5:
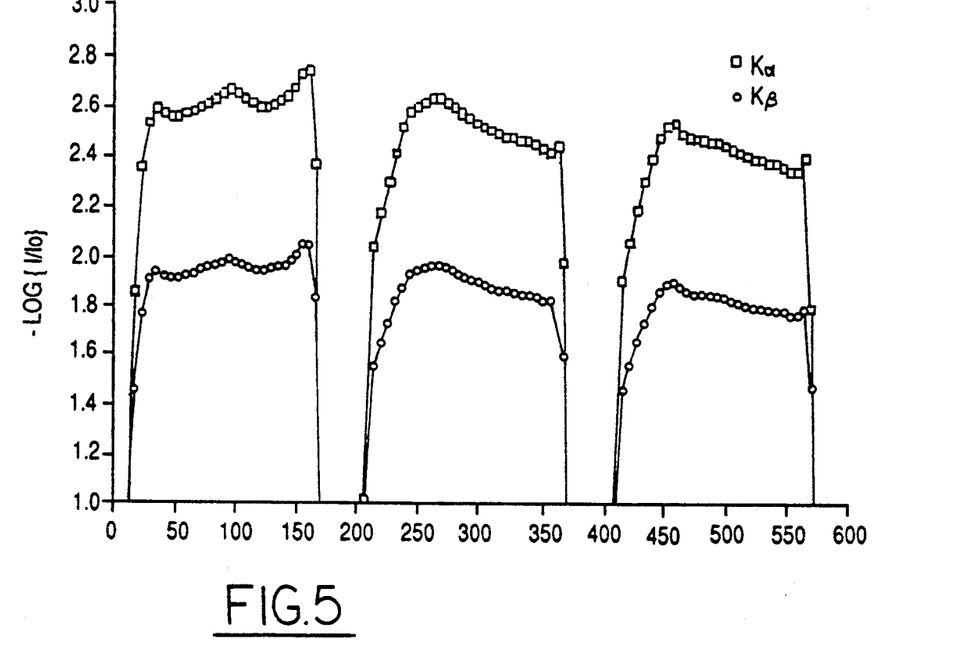
FIG. 5 is a diagram showing relative attenuation scans of washcoated ceramic catalytic converters.

Converter scans plotted in FIG. 5 are the scans of the three coated ceramic converters (substrates) using the Pb x-ray technique. The first converter, D218, shows a relatively uniform washcoat distribution, but the remaining two, D206 and D2, show a large drop in attenuation on the front end of the converter. The same converters were then profiled using the comparative established (single attenuation) method for measuring washcoat coating distributions.

Figure 6:
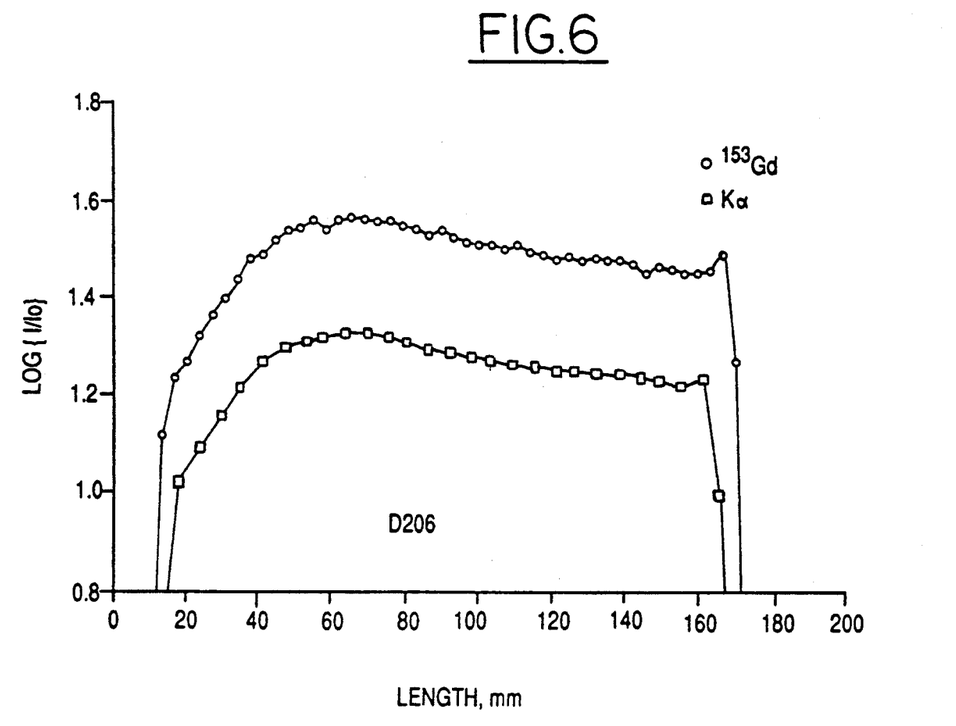
FIG. 6 is a diagram showing a comparison of a single attenuation method using Gd-153 and the Pb (lead) Kα scan of the invention.

The method of the invention compared favorably to the comparative single attenuation method currently used (FIG. 6). The Pb-Ka profile portion produced by the Pb x-ray technique of the invention provided a profile similar to that of the comparative method used to scan for washcoat distribution. Thus, the method of the invention may be used to determine the washcoat distribution, as well as to determine the presence of platinum (FIG. 6).

Figure 7:
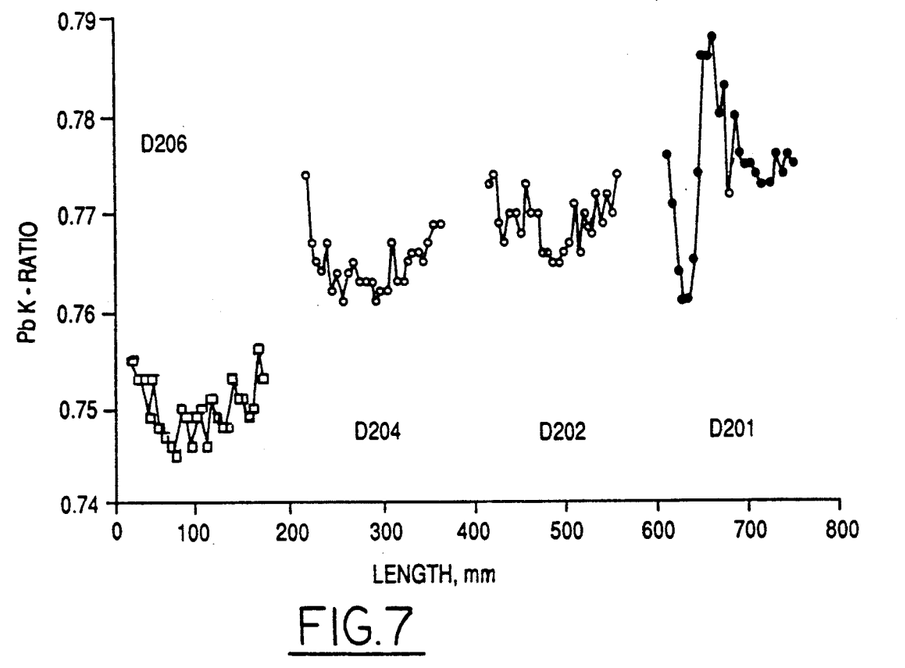
FIG. 7 is a diagram showing Pb K-ratios of a ceramic washcoated substrate having no catalysts and three ceramic washcoated substrates containing catalysts.
Figure 8:
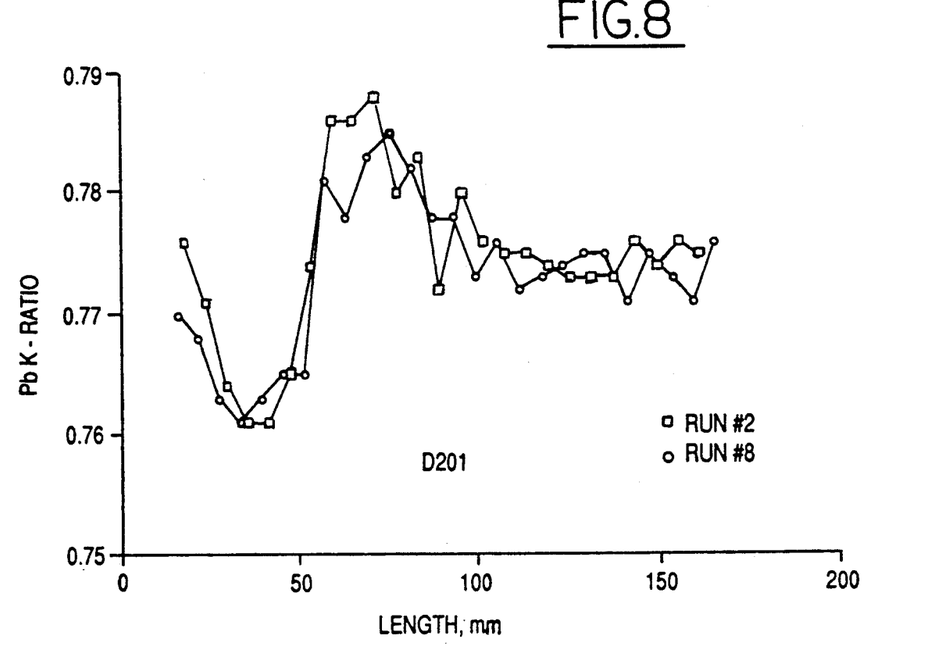
FIG. 8 is a diagram showing repeat scans on one of the converters shown in FIG. 7 (D201).

Shown in FIG. 7 are the Pb K-ratio scans of three ceramic converters (D204, D202, and D201) with the alumina-ceria substrate and platinum catalyst along with a converter of similar washcoat weight (D206) having no catalyst. The change is Pb K-ratio is clearly evident for the catalysts having platinum present. Repeat scans on converter D201 as shown in FIG. 8 confirm the indication of significant platinum nonuniformity near the front of converter 201.

Figure 9:
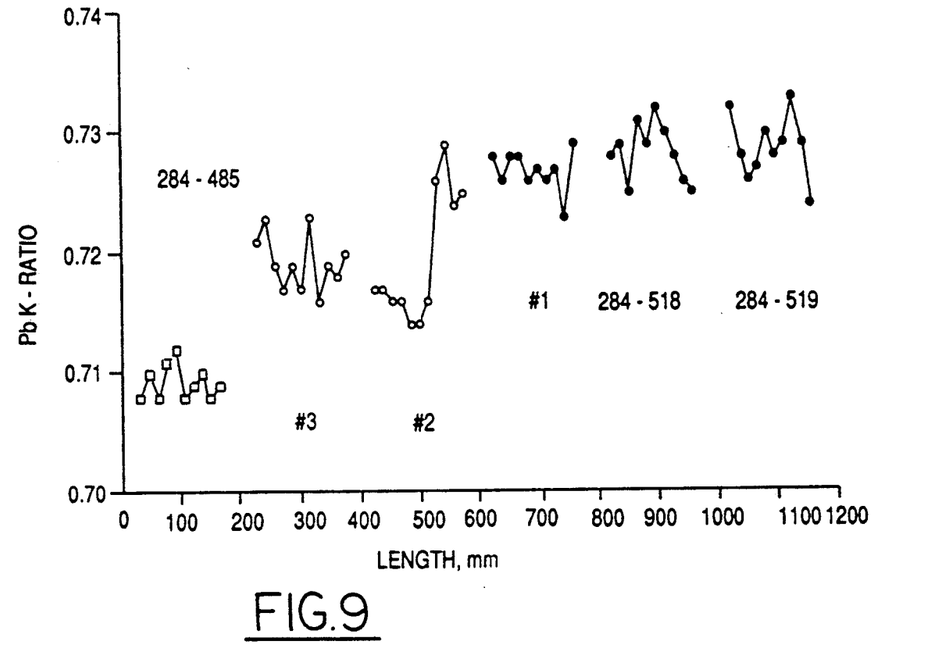
FIG. 9 is diagram showing Pb K-ratios for a washcoated metal foil monolith converters without catalysts and metal foil monolith converters with catalysts.
Figure 10:
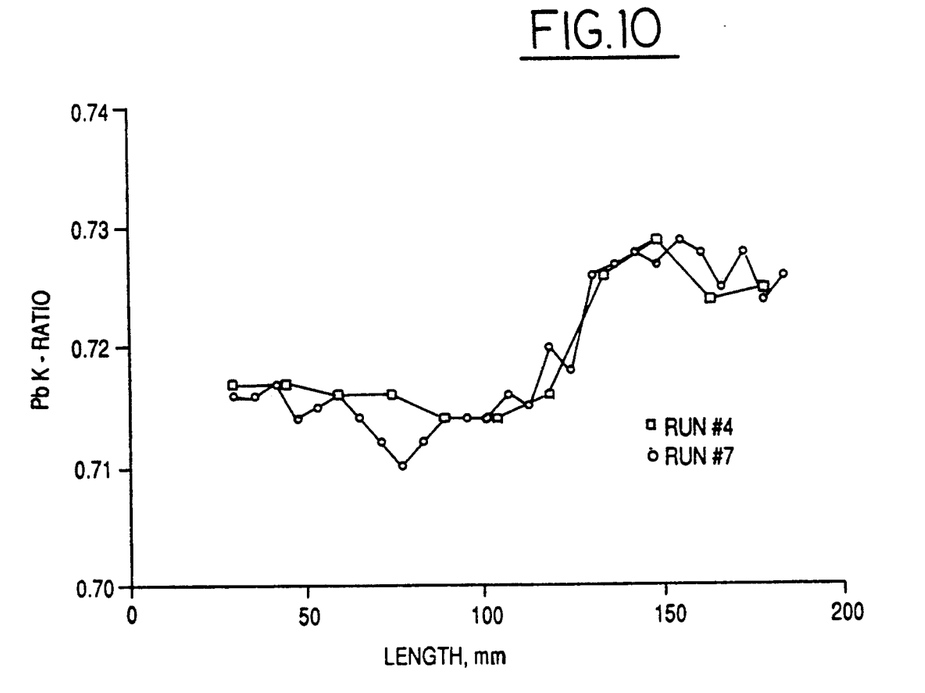
FIG. 10 is a diagram showing repeat scans on one of the converters shown in FIG. 7 (#2).

FIG. 9 shows the Pb K-ratios for washcoated MFM converter (284-485) and for the MFM converters washcoated and with platinum catalysts (Nos. 3, 2, 1, 284-518 and 284-519). The repeat scan of converter #2 as shown in FIG. 10 was done to confirm the wide variation in the K-ratio. All the MFM converters showed uniformed washcoat distribution.

The average K-ratios for all converters scanned are presented in Tables 3 and 4.

TABLE 3

Pb K-Ratios For Ceramic Substrates

| Substrate Number | Run | Pb K-ratio | Delta K-Ratio |
|---|---|---|---|
| D2 | 1 | .7508 | — |
| D2 | 3 | .7506 | — |
| D218 | 1 | .7473 | — |
| D218 | 3 | .7467 | — |
| D206 | 1 | .7495 | — |
| D206 | 2 | .7499 | — |
| D206 | 3 | .7489 | — |
| D206 | 8 | .7487 | — |
| D206 | 9 | .7478 | — |
| D201 | 2 | .7746 | .0247 |
| D201 | 3 | .7729 | .0240 |
| D201 | 8 | .7733 | .0246 |
| D202 | 2 | .7693 | .0194 |
| D202 | 3 | .7678 | .0189 |
| D204 | 2 | .7649 | .0150 |
| D204 | 3 | .7623 | .0134 |
| D204 | 9 | .7628 | .0150 |

TABLE 4

Pb K-Ratios For MFM Substrates

| Substrate Number | Run | Pb K-ratio | Delta K-Ratio |
|---|---|---|---|
| 285-033 | 6 | .7086 | — |
| 284-485 | 6 | .7094 | — |
| 284-485 | 4 | .7105 | — |
| 284-485 | 5 | .7095 | — |
| 284-485 | 7 | .7086 | — |
| 284-485 | 10 | .7085 | — |
| 284-518 | 6 | .7283 | .0189 |
| 284-519 | 6 | .7288 | .0194 |
| 284-519 | 5 | .7286 | .0191 |
| #1 | 4 | .7275 | .0170 |
| #1 | 6 | .7268 | .0174 |
| #2 | 4 | .7211 | .0106 |
| #2 | 6 | .7194 | .0100 |
| #2 | 7 | .7193 | .0107 |
| #3 | 5 | .7198 | .0103 |
| #3 | 6 | .7192 | .0098 |
| #3 | 10 | .7185 | .0100 |

Figure 11:
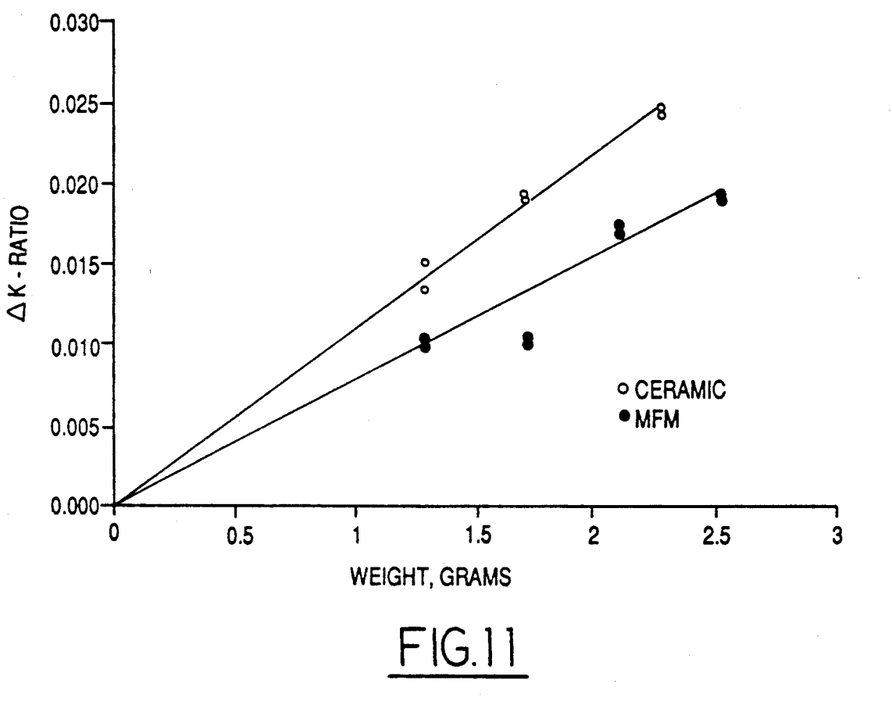
FIG. 11 is a diagram showing the change in Pb K-ratios as a function of platinum weight for ceramic and metal foil monolith converters.

The K-ratios vary on a run-to-run basis, which is likely due to different detector positions and source intensity. However, the relative differences between converters with platinum catalysts and converters with washcoat only were consistent throughout. The delta K-ratios are plotted in FIG. 11 against the known platinum weights for both ceramic and MFM converters. There is an excellent correlation between the delta K-ratio and platinum weight for the ceramic converters, including the converter with the platinum maldistribution (No.201). The correlation is not quite as good with the MFM converters which may be influenced by the nonuniformity in converter #2. Importantly, the procedure provides good repeatability for each converter.

In order to determine the accuracy of the Pb x-ray method, repeat measurements were made at a single location on several converters. The four converters chosen were D206, D204, 284-845 and #3; that is, two ceramic and two MFM, one each containing washcoat and one each containing washcoat and platinum catalysts. Repeat measurements were taken through the center of each converter by keeping the moving tray stationary. The results of these studies are shown in Table 5.

TABLE 5

Precision Data for Ceramic and MFM substrates

| Substrate Type | No. | Pt | No. of Counts | Average Pb K-ratio | Standard Deviation |
|---|---|---|---|---|---|
| Ceramic | D206 | No | 28 | .7471 | .0018 |
| Ceramic | D204 | Yes | 24 | .7615 | .0016 |
| MFM | 284-485 | No | 29 | .7079 | .0016 |
| MFM | #3 | Yes | 22 | .7174 | .0012 |

Standard deviations for the resulting delta K-ratios are 0.0024 and 0.0020, respectively, for ceramic and MFM converter measurements. This corresponds to a standard deviation of approximately 10 percent (20 percent uncertainty at the 95 percent confidence level) in the platinum determination for each measurement by use of correlation shown in FIG. 11.

By the method of the invention, for an entire converter, platinum level uncertainties at the 95 percent confidence level were less than 7 percent for run #4 and less than 5 percent for run #7 for converter #2 as shown in FIG. 10.

In the method of the invention, the radiation energy components may be generated separately or simultaneously. If they are generated simultaneously, they must be measured concurrently, thereby requiring the radiation detector to have a high enough energy resolution to distinguish between Ka and Kb components. This is most advantageously done by using a liquid nitrogen-cooled semiconductor detector.

Advantageously, the relative intensities of all x-rays are fixed and depend only on the geometry of the system and intensity of the Gd-153 excitation source. Therefore, the intensity measurements need not be corrected for source decay. Advantageously, the method of the invention is nondestructive while at the same time being specific for determination of the quantity and distribution of platinum in ceramic and metal foil monolith converters and on any other substrate or object.

Advantageously, a one-hour scan can provide a determination of the distribution profile of platinum and the total platinum loading with accuracy better than plus or minus ($\pm$) 10 percent at a 95 percent confidence level. This is achieved, in part, because the radiation energy components and radiation intensity expressions provided by the method and apparatus of the invention permit platinum determination with minimal interference by variations in converter substrate weight, coating weight, and coating composition.

Measurements shown above demonstrated that on a series of converters, changes in the radiation intensities expression were directly proportional to the amount of platinum present.

Repeatable platinum distribution patterns were obtained by axial scans of both ceramic and metal foil monolith type converters. In as little as one hour, it was possible to determine distribution of platinum nondestructively by the single radiographic method of the invention comprising only a single radiation source and a single scan.

Although the method has been described in a preferred embodiment with respect to the determination of platinum carried by a catalytic converter, the method may also advantageously be used to determine the presence, profile and loading of an object to determine other elements such as iridium, gold and mercury which also have a mass absorption edge which is bracketed by the energies of the two x-ray components. Thus, the method and apparatus may conveniently be used to assay gold coins and other objects.

While this invention has been described in terms of certain embodiments thereof, it is not intended that it be limited to the above description but rather only to the extent set forth in the following claims.

The embodiments of the invention in which an exclusive property or privilege is claimed are defined as follows:

1. A method for determining a distribution of platinum, dispersed on a carrier providing a catalyst for treating exhaust from a vehicle engine, comprising:
    (a) generating essentially simultaneously x-rays of lead consisting of first and second energy components by fluorescence of the lead with a source of radiant energy greater than a K-absorption edge characteristic of the lead, one of the components being above and the other component being below the K-absorption edge characteristic of platinum;
    (b) directing the x-rays onto the carrier to cause the x-rays to be incident on the carrier at a first location and at a second location spaced from the first location; and
    (c) determining a relative attenuation of the first and second energy components at each one of the first and second locations, and then determining any difference in the relative attenuations between the first and second locations proportional to relative amounts of platinum at the first and second locations.

2. A method according to claim 1 wherein the source of radiant energy consists essentially of at least one selected from the group consisting of gadolinium-153 and cobalt-57.

3. A method according to claim 1 further comprising determining the relative attenuation by:
    (a) monitoring any difference in intensity of each of the energy components, respectively, from a first respective intensity to a second respective intensity;
    (b) determining a first attenuation of the first energy component proportional to a log of a ratio of the second intensity to the first intensity of the first energy component;
    (c) determining a second attenuation of the second energy component proportional to the log of the ratio of the second intensity to the first intensity of the second energy component; and
    (d) determining the relative attenuation proportional to the ratio of the first and second attenuations.

4. A method for determining an unknown amount of platinum dispersed on a carrier, based upon a known quantity of platinum comprising:
    a) generating essentially simultaneously x-rays of lead having two energy components, a first component being above and a second component being below a K-absorption edge characteristic of platinum, by fluorescence of the lead with at least one selected from the group consisting of gadolinium-153 and cobalt-57 to provide radiant energy greater than a K-absorption edge characteristic of the lead;

b) directing the x-rays onto the carrier to cause the x-rays to be incident on any desired location of the carrier;

c) determining a relative attenuation of the two energy components of lead x-rays incident on the location of the carrier;

d) determining the relative attenuation caused by the known quantity of platinum; and e) determining an amount of platinum on the location proportional to the relative attenuation caused by the unknown amount based upon the relative attenuation caused by the known quantity.

5. A method for determining an amount of at least one metal selected from the group consisting of gold, platinum, iridium and mercury, comprising:

(a) generating essentially simultaneously x-rays of lead consisting of first and second energy components by fluorescence of the lead with a source of radiant energy greater than a K-absorption edge characteristic of the lead, at least one of the component being above and the other component being below the K-absorption edge characteristic of the metal to be detected;

(b) directing the x-rays onto a surface of a substance to cause the x-rays to be incident thereon;

(c) determining relative attenuation of at least two energy components of lead x-rays by the substance proportional to an amount of the metal.

6. A method according to claim 5 wherein the metal is platinum.

7. A method according to claim 5 wherein the source of radiant energy consists essentially of at least one selected from the group consisting of gadolinium-153 and cobalt-57.

8. A method according to claim 5 further comprising determining the relative attenuation by:

(a) monitoring any difference in intensity of each of the energy components, respectively, from a first respective intensity to a second respective intensity;

(b) determining a first attenuation of the first energy component proportional to a log of a ratio of the second intensity to the first intensity of the first energy component;

(c) determining a second attenuation of the second energy component proportional to the log of the ratio of the second intensity to the first intensity of the second energy component; and (d) determining the relative attenuation proportional to the ratio of the first and second attenuations.

* * * * *